United States Patent
Llas Vargas et al.

(10) Patent No.: US 10,105,170 B2
(45) Date of Patent: Oct. 23, 2018

(54) STERNAL CLOSURE ASSEMBLY

(71) Applicant: Neos Surgery, S.L., Cerdanyola del Valles (ES)

(72) Inventors: Salvador Llas Vargas, Espanya (ES); Pau Garcia Roig, Girona (ES); Marc Serrahima Tornel, Catalunya (ES)

(73) Assignee: NEOS Surgery, Cerdanyola del Valles (ES)

( * ) Notice: Subject to any disclaimer, the term of this patent is extended or adjusted under 35 U.S.C. 154(b) by 331 days.

(21) Appl. No.: 14/971,294

(22) Filed: Dec. 16, 2015

(65) Prior Publication Data
US 2017/0172636 A1 Jun. 22, 2017

(51) Int. Cl.
*A61B 17/68* (2006.01)
*A61B 17/82* (2006.01)
*A61B 17/80* (2006.01)

(52) U.S. Cl.
CPC ............ *A61B 17/823* (2013.01); *A61B 17/68* (2013.01); *A61B 17/8076* (2013.01)

(58) Field of Classification Search
CPC .............. A61B 17/8076; A61B 17/823; A61B 17/8009; A61B 17/68
See application file for complete search history.

(56) References Cited

U.S. PATENT DOCUMENTS

| 5,928,231 A | * | 7/1999 | Klein | .................. | A61B 17/823 606/218 |
| 6,051,007 A | * | 4/2000 | Hogendijk | ............. | A61B 17/08 606/151 |
| 7,635,364 B2 | * | 12/2009 | Barrall | ............... | A61B 17/7059 606/70 |
| 7,803,176 B2 | | 9/2010 | Teague et al. | | |

(Continued)

FOREIGN PATENT DOCUMENTS

| CN | 103211632 A | 7/2013 |
| CN | 203988322 U | 12/2014 |

(Continued)

OTHER PUBLICATIONS

International Search Report in corresponding International Application No. PCT/EP2016/081129, dated Feb. 23, 2017.

*Primary Examiner* — David Bates
(74) *Attorney, Agent, or Firm* — Edell, Shapiro & Finnan, LLC

(57) ABSTRACT

A sternal closure assembly for securing first and second lateral halves of a sternum. The assembly includes a first sliding body having a female portion and a second sliding body having a male portion, the male portion being telescopically mateable with the female portion. The male portion is capable of being fully introduced into the female portion only upon there being an elastic deformation of at least a part of at least one of the male and female portions, the male and female portions configured such that when the (Continued)

second body is mated with the first body the elastic deformation results in a forceful engagement between the male and female portions and also a forceful engagement between a first set of non-deforming teeth extending upward from an interconnecting bridge member of the first sliding body and a second set of non-deforming teeth extending upward from an interconnecting bridge member of the second sliding body.

22 Claims, 16 Drawing Sheets

(56) References Cited

U.S. PATENT DOCUMENTS

| | | |
|---|---|---|
| 8,366,754 B2 | 2/2013 | Teague et al. |
| 8,556,948 B2 | 10/2013 | Teague et al. |
| 8,758,417 B2 | 6/2014 | Anderson et al. |
| 8,936,628 B2 | 1/2015 | Anderson |
| 2003/0083694 A1* | 5/2003 | Miller, III ............ A61B 17/823 606/216 |
| 2003/0130661 A1* | 7/2003 | Osman ............... A61B 17/7059 606/71 |
| 2005/0267475 A1* | 12/2005 | Miller, III ............ A61B 17/823 606/324 |
| 2006/0167458 A1* | 7/2006 | Gabele ................ A61B 17/823 606/916 |
| 2007/0043371 A1* | 2/2007 | Teague ............... A61B 17/8076 606/71 |
| 2009/0118774 A1* | 5/2009 | Miller, III ............ A61B 17/823 606/324 |
| 2009/0125073 A1* | 5/2009 | Rehm .................. A61B 17/823 606/324 |
| 2009/0138054 A1* | 5/2009 | Teague ............... A61B 17/8076 606/324 |
| 2010/0198221 A1* | 8/2010 | Hearn ................ A61B 17/8009 606/71 |

FOREIGN PATENT DOCUMENTS

| | | |
|---|---|---|
| CN | 204446068 U | 7/2015 |
| DE | 8222027 U1 | 11/1982 |
| DE | 102007052315 A1 | 5/2009 |

\* cited by examiner

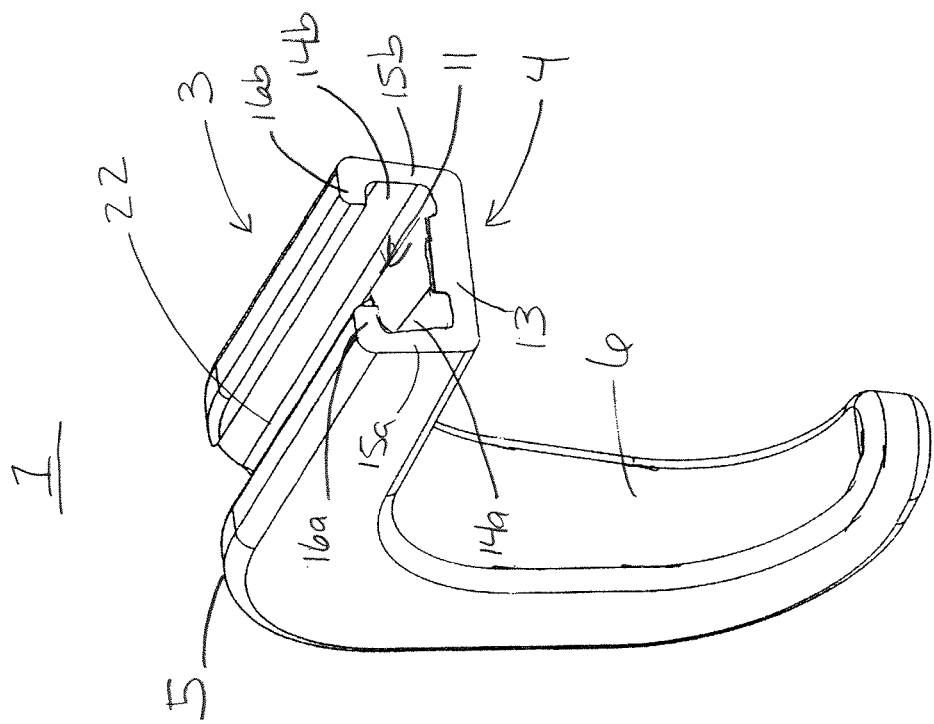
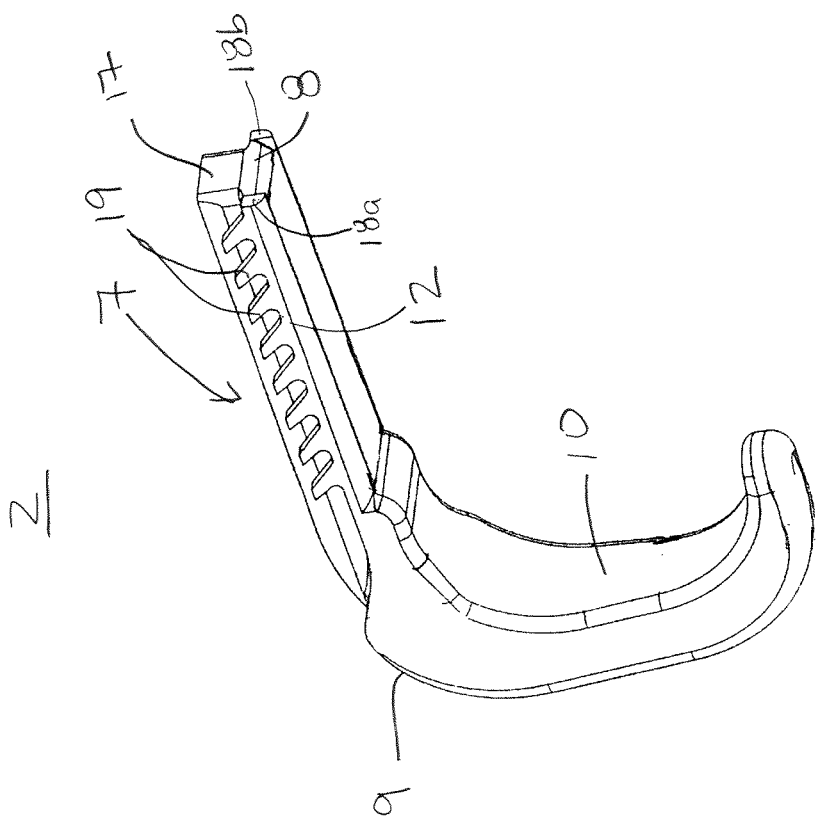

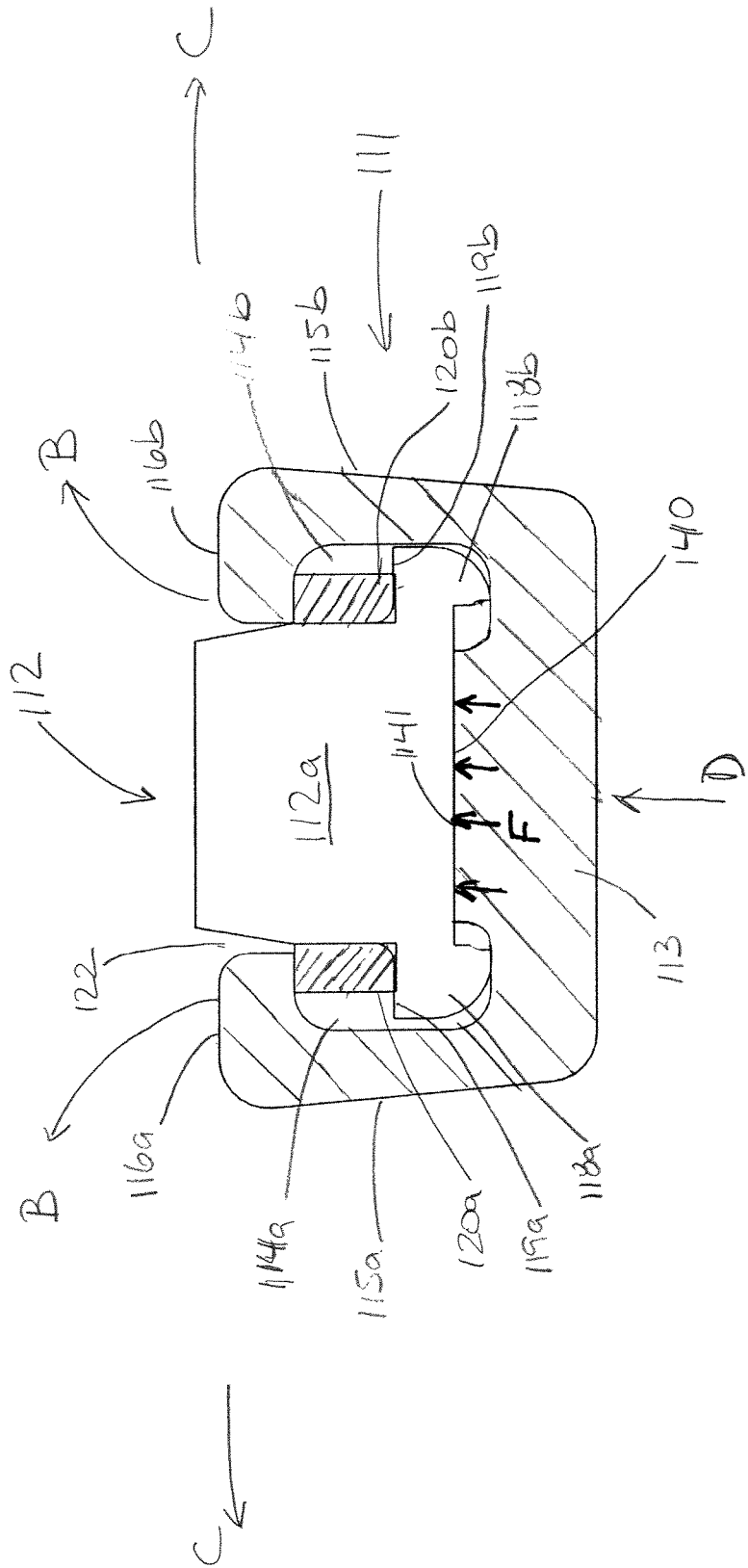

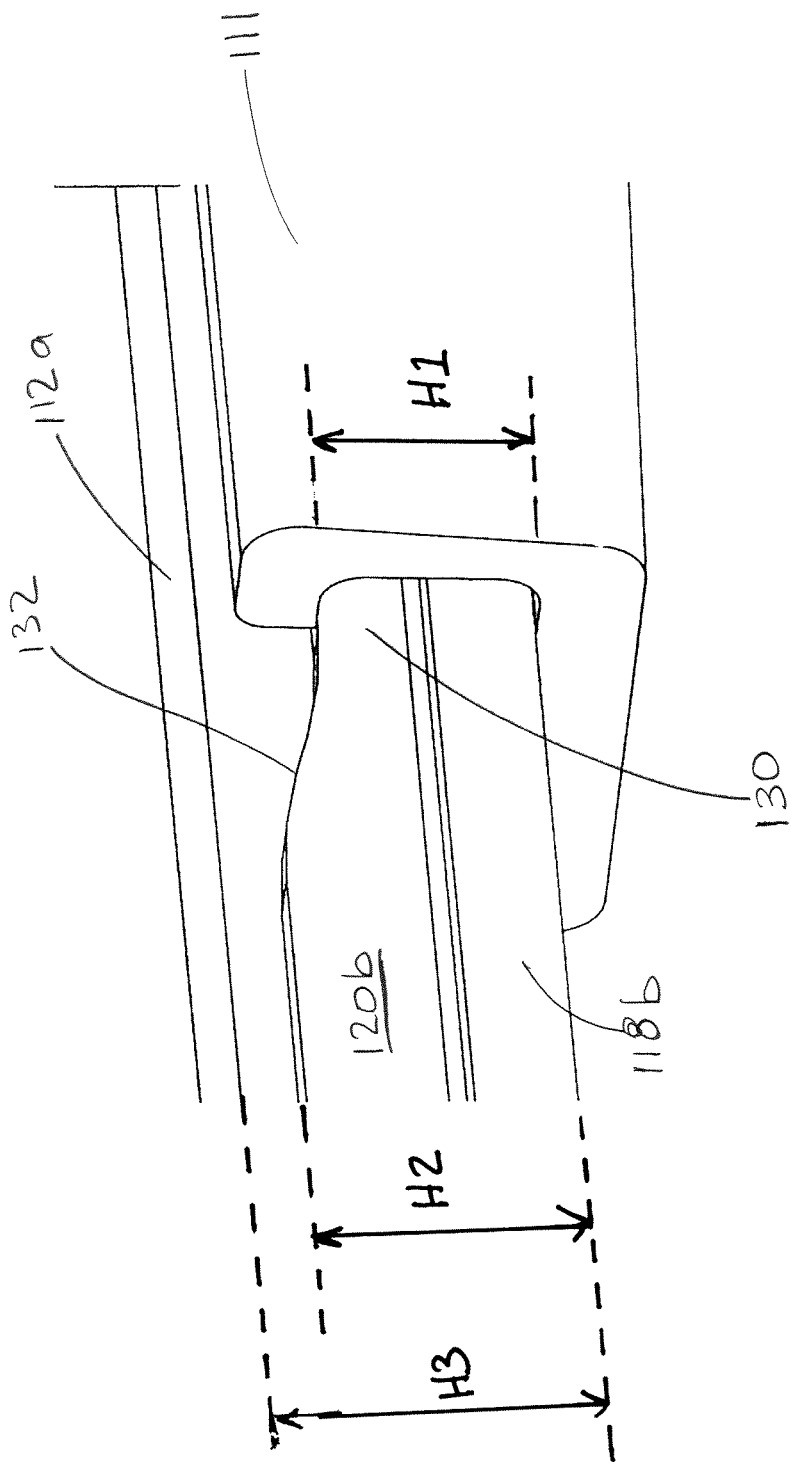

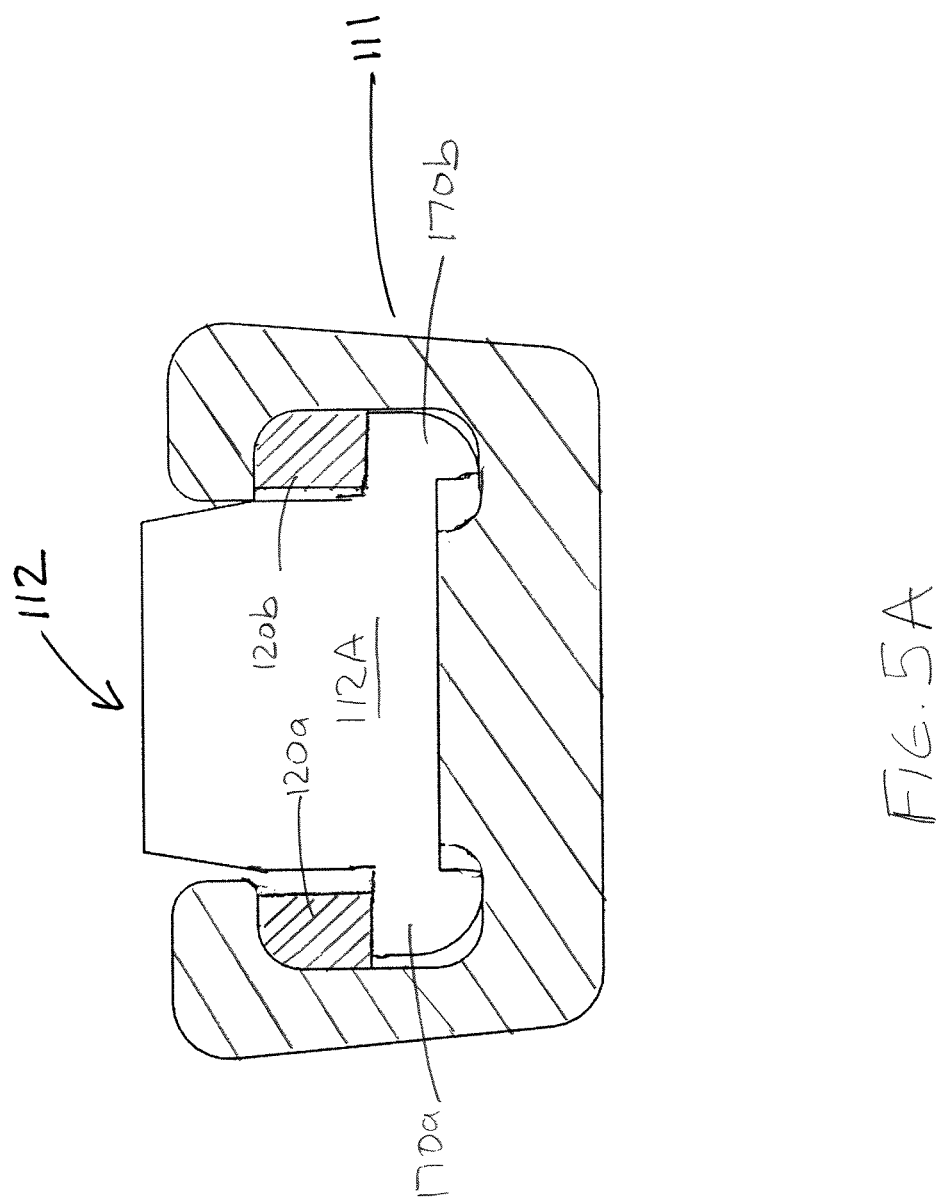

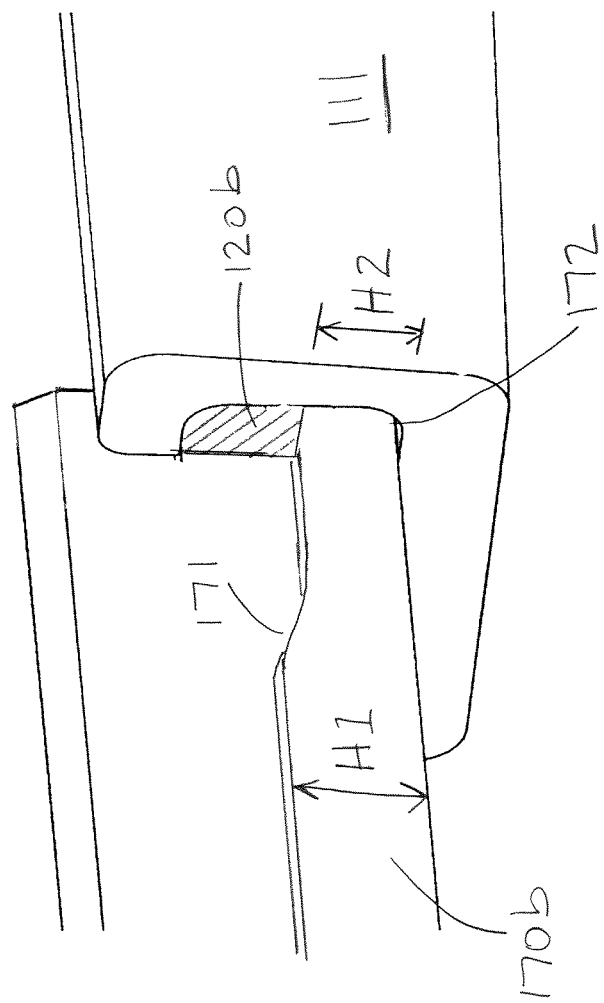

STERNAL CLOSURE ASSEMBLY

TECHNICAL FIELD

The present invention relates to an assembly for securing together first and second lateral halves of a sternum that has been longitudinally severed.

BACKGROUND

U.S. Pat. No. 8,936,628 discloses a sternal clamp assembly having a first sliding body member and a second sliding body member that are telescopically mated so as to be securable about a severed sternum. The first and second sliding body members are secured together by a suture that encircles the first and second sliding members. The method by which the first and second sliding members are secured together requires a part (i.e. suture) apart from the first and second members, and the time consuming and tedious task of carefully assembling the suture about the assembly.

It is an object of the present invention to provide a method of assisting in securing together telescopically mateable first and second sliding members of a sternal closure assembly.

SUMMARY OF THE DISCLOSURE

According to one implementation a sternal closure assembly for securing first and second lateral halves of a sternum that has been longitudinally severed is provided, the sternal closure assembly comprising: a first sliding body including a first interconnecting bridge member and at least one leg extending downwardly from the first interconnecting bridge member, the at least one leg configured to abut an exterior edge of the first lateral halve of the sternum, the first interconnecting bridge member including a female portion; and a second sliding body telescopically mateable with the first sliding body, the second sliding body including a second interconnecting bridge member and at least one leg extending downwardly from the second interconnecting bridge member, the at least one leg configured to abut an exterior edge of the second lateral halve of the sternum, the second interconnecting bridge member including a male portion, the male portion capable of being fully introduced into the female portion only upon there being an elastic deformation of at least a part of at least one of the male and female portions, the male and female portions configured such that when the second body is mated with the first body the elastic deformation results in a forceful engagement between the male and female portions to assists in holding the second sliding body on the first sliding body. Thus, internally generated forces created by the act of telescopically mating the first and second sliding bodies function to assist in holding the second sliding body on the first sliding body.

According to another implementation a sternal closure assembly is provided for securing first and second lateral halves of a sternum that has been longitudinally severed, the sternal closure device comprising: a first sliding body member including a first interconnecting bridge member and at least one leg extending downwardly from the first interconnecting bridge member, the at least one leg configured to abut an exterior edge of the first lateral halve of the sternum, the first interconnecting bridge member having a length and comprising a female portion, the female portion delimited in part by a base of the first interconnecting bridge member, the base including a top side comprising a plurality of upward projecting teeth arranged substantially transverse to the length of the first interconnecting bridge member; and a second sliding body telescopically mateable with the first sliding body, the second sliding body including a second interconnecting bridge member and at least one leg extending downwardly from the second interconnecting bridge member, the at least one leg configured to abut an exterior edge of the second lateral halve of the sternum, the second interconnecting bridge member having a length and comprising a male portion, the second interconnecting bridge member having a bottom side comprising a plurality of downward projecting teeth engageable with the plurality of upward projecting teeth, the plurality of downward projecting teeth arranged substantially transverse to the length of the second interconnecting bridge member, when the first and second sliding members are mated, or being telescopically mated, the plurality of upward projecting and downward projecting teeth are configured to engage with one another in a manner that only permits a telescopic shortening of the sternal closure assembly without there being a change in the position of the plurality of upward projecting teeth in relation to the base of the first interconnecting bridge member nor a change of position of the plurality of downward projecting teeth in relation to the bottom side of the second interconnecting bridge member, the male portion capable of being introduced into the female portion only upon there being an elastic deformation of at least a part of at least one of the male and female portions, the male and female portions configured such that when the second sliding body is mated with the first sliding body the elastic deformation results in a forceful engagement between the male and female portions and also in a forceful engagement between the plurality of upward projecting teeth and downward projecting teeth.

BRIEF DESCRIPTION OF THE DRAWINGS

FIG. 1A shows a perspective view of a first sliding body of a sternal closure assembly according to one implementation, the first sliding body including an interconnecting bridge member having a female portion.

FIG. 1B shows a perspective view of a second sliding body of a sternal closure assembly according to one implementation, the second sliding body including an interconnecting bridge member having a male portion.

FIG. 4A shows a cross-section view of female and male portions according to another implementation.

FIG. 4B shows an enlarged partial perspective view of the female and male portions shown in FIG. 4A.

FIG. 5A shows a cross-section view of female and male portions according to another implementation.

FIG. 5B shows an enlarged partial perspective view of the female and male portions shown in FIG. 5A.

DETAILED DESCRIPTION

Figure 2A:
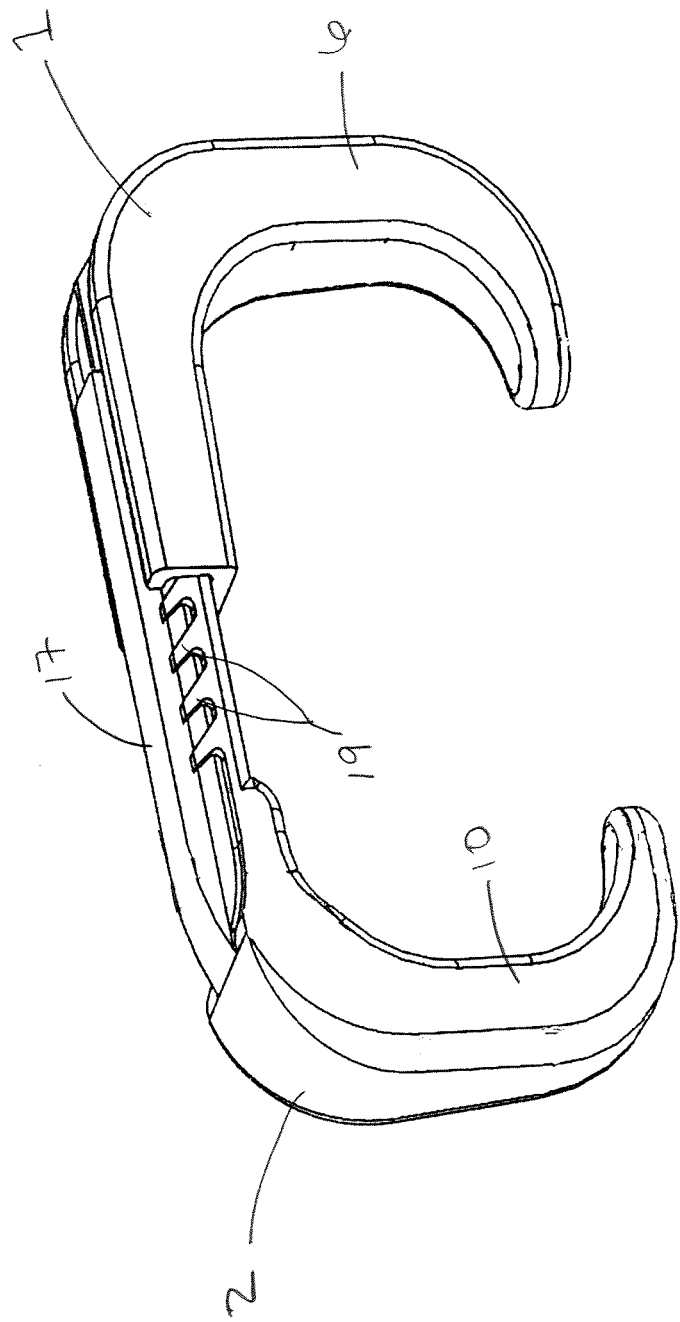
FIG. 2A shows a perspective view of the first and second sliding bodies depicted in FIGS. 1A and 1B being telescopically mated.

FIGS. 1A and 1B show perspective views of first and second sliding bodies of a sternal closure assembly according to one implementation. The first and second sliding bodies are configured for securing first and second lateral halves of a sternum that has been longitudinally severed. First sliding body 1 includes an interconnecting bridging member 3 having a leading end 4 and a trailing end 5. Extending downwardly from the trailing end 5 is a leg 6, the leg 6 being configured to abut an exterior edge of the first lateral halve of the sternum. Second sliding body 2 includes an interconnecting bridging member 7 having a leading end 8 and a trailing end 9. Extending downwardly from the trailing end 9 is a leg 10, the leg 10 being configured to abut an exterior edge of the second lateral halve of the sternum. As shown in FIG. 2, the first and second sliding bodies 1 and 2 are adapted to be telescopically joined so that in practice the legs 6 and 10 can be moved relative to one another to effectuate a securing of the first and second halves of the severed sternum between the legs.

The interconnecting bridging member 3 of the first sliding body 1 comprises a female portion 11 that is adapted to receive a male portion 12 comprised in the interconnecting bridging member 7 of the second sliding body 2. In the implementation of FIGS. 1-4 the female portion 11 includes two opposing facing channels 14a and 14b. Channel 14a is delimited by a portion of the base 13 of the interconnecting bridging member 3 and first and second walls 15a and 16a. Channel 14b is delimited by a portion of the base 13 of the interconnecting bridging member 3 and first and second walls 15b and 16b. Each of walls 15a and 15b extend in an upward direction from the base 13 with each of the walls 16a and 16b being respectively connected to walls 15a and 15b and extending over at least a portion of the base 13. According to one implementation, walls 15a, 16a and walls 16b, 16b form L-shaped members as shown in the figures, with the walls 15a and 15b arranged substantially orthogonal to the base 13. It is important to note that the wall or walls that form the channels 14a and 14b may comprise other shapes and angular orientations.

Figure 2B:
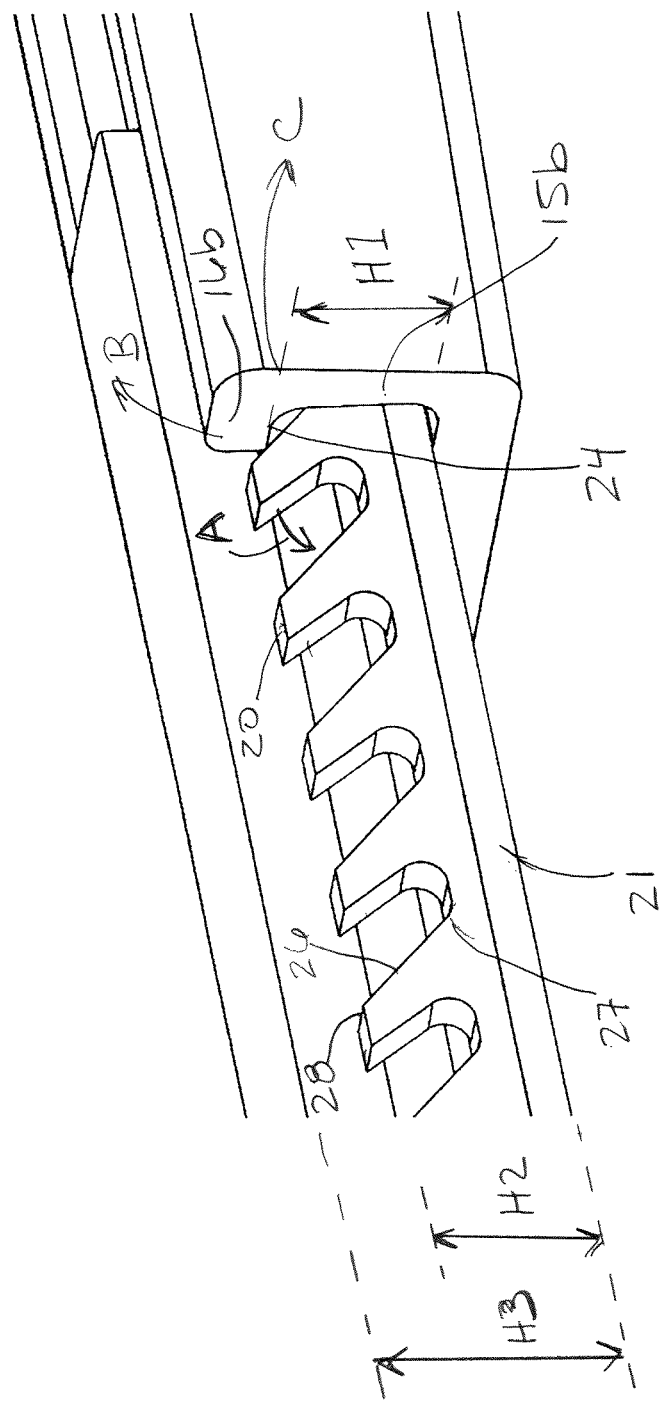
FIG. 2B shows an enlarged partial perspective view of the female and male portions depicted in FIGS. 1A and 1B as the first and second sliding bodies are being telescopically mated.
Figure 3:
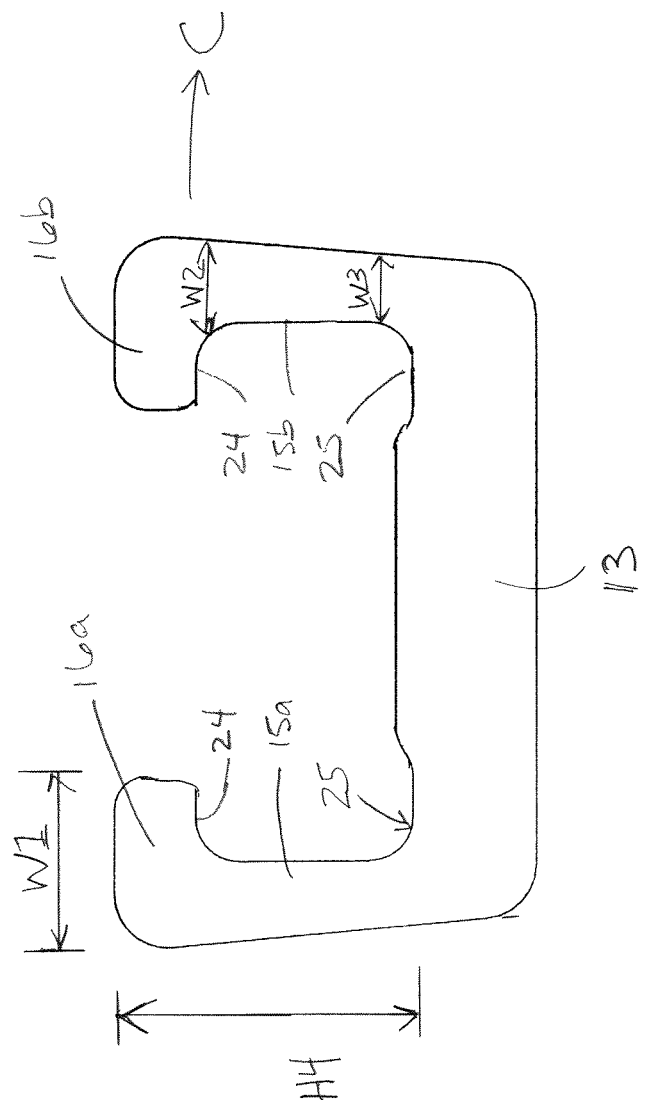
FIG. 3 shows a cross-section of the female portion depicted in FIGS. 1 and 2.

According to one implementation the male portion 12 includes a central body 17 with first and second flange sections 18a and 18b extending from opposite sides of the central body. Each of the first and second flange sections 18a and 18b includes a plurality of spaced-apart tabs 19 that extend upwardly from a base 21 of each of the flanges 18a and 18b. As shown in FIGS. 2A and 2B, prior to the male portion 12 being introduced into the female portion 11 the height H1 of the channels 14a and 14b in the female portion 11 is less than the height H2 of the apex 20 of the tabs 19 as measured from a bottom of the base 21 of the male portion 12. As shown in FIGS. 1-3, according to some implementations, the central body 17 of the male portion 12 resides within a central cavity 22 of the female portion 11 and has a height H3 greater than the height H1. According to some implementations the width of the central body 17 is slightly less than or equal to the width of the cavity 22 when the female portion is not assembled with the male portion 12. This height and width characteristic of the central body 17 can assists in maintaining a longitudinal alignment of the male portion 12 with the female portion 11 as the first and second sliding bodies 1 and 2 are telescopically mated.

According to one implementation the tabs 19 are capable of being elastically deformed so that they flex in a downward direction A as they are introduced into the confined space of the channels 14a and 14b as shown in FIG. 2B. As a result of the resilient characteristic of the tabs 19, in that they are internally urged to at least in part assume their original shape, a forceful engagement between the female and male portions 11 and 12 is achieved to assist in holding the second sliding body 2 onto the first sliding body 1.

According to some implementations the female portion 11 is constructed such that the channels 14a and 14b substantially maintain their shape when the tabs 19 of the male portion 12 are introduced into the channels. According to other implementations the female portion is constructed to also elastically deform with one or more of the walls that form the channels 14a, 14b bending upward or outward as the tabs 19 are introduced into the channels. For example, as shown in FIG. 2B, wall 16b of channel 14b may bend resiliently upward in the direction B and/or wall 15b may bend resiliently outward in the direction C. The same is true with the walls 15a and 15b of channel 14a.

According to other implementations the tabs 19 are not deformable when they are introduced into the channels 14a, 14b of the female portion 11. According to such implementations the female portion 11 is constructed to elastically deform with one or more of the walls that form the channels 14a, 14b bending upward or outward as the tabs 19 are introduced into the channels. For example, wall 16b of channel 14b may bend resiliently upward in the direction B and/or wall 15b may bend resiliently outward in the direction C in a manner like that shown in FIG. 3. The same is true with the walls 15a and 15b of channel 14a.

According to some implementations, as shown in FIGS. 1 and 2, the tabs 19 have a leading edge 26 in the form of a ramp. The ramp has a leading end 27 and a trailing end 28 with the height of the leading end being less than the height of the trailing end. The ramped configuration allows for an incremental versus an abrupt introduction of each of the tabs 19 into the respective channels 14a,14b of the female portion 11. The inclusion of a ramp makes it easier to introduce the tabs 19 into the channels 14a, 14b as the second sliding body 2 is mated with the first sliding body 1.

The inclusion of the ramp also reduces the likelihood of the tabs 19 breaking as they are introduced into the channels 14a, 14b.

According to some implementations each of the first and second sliding bodies 2 is a unitary structure, each made of a single part, by for example a molding process. According to some implementations, the tabs 19 of the male portion 12 are formed separately and then attached to the second sliding body 2 by an adhesive, thermal welding, etc.

FIG. 3 shows a cross-section of the intersecting bridge member 3 that comprises the female portion 11. According to some implementations, as shown in FIG. 3, the upper wall surface 24 and lower wall surface 25 of each of the channels 14a and 14b is substantially devoid of undulations or other features that would act to impede a joining of the male portion 12 with the female portion 11. This advantageously minimizes the amount of force required to mate the first and second sliding bodies. As noted above, according to some implementations one or more of the walls 15a and 15b may be configured to bend resiliently outward and/or one or more of the walls 16a and 16b may be configured to resiliently bend upward upon the male and female portions being mated. According to some implementations, to facilitate an outward bending of walls 15a and 15b in the direction C the height dimension H1 of channels 14a and 14b is selected to be least one and one half (1.5) times greater than the width dimension W1 of the respective walls 16a and 16b. A bending outward of walls 15a and 15b in the direction C may also be facilitated by constructing the walls to have a reduced width dimension W2 at or near a base of the walls as compared to the width dimension W3 at or near the top of the walls 15a, 15b.

In the examples above and below, the female portion 11 is disclosed as possessing at least two channels for receiving two complementary parts of a male portion 12. For example, in the foregoing disclosure the female portion 11 is described as possessing first and second channels 14a, 14b that respectively receive a set of tabs 19 arranged on opposite sides of the male portion 12. It is contemplated, however, that the female portion 11 may comprise less than or greater than two channels for receiving less than or greater than two complementary parts of the male portion 12. This is true for each of the implementations disclosed or contemplated herein.

With continued reference to FIGS. 1-3, as noted above, each of the first and second sliding bodies 1 and 2 may comprise a unitary construction by, for example, being injection molded as a single part. According to such an implementation one or both of the first and second bodies 1 and 2 may be molded from a material that is capable of at least in part being elastically deformed. The material may be, for example, polyether ether ketone (PEEK).

FIGS. 4-7 illustrate male and female portions of a sternal closure assembly according to other implementations. These female and male portions are respective substitutes to the female portion 11 and male portion 12 of the sternal closure assembly of FIGS. 1-3 described above.

FIG. 4A shows a female portion 111 having a construction similar to that of female portion 11 described above. The female portion 111 includes two opposing facing channels 114a and 114b. Channel 114a is delimited by a portion of the base 113 of the interconnecting bridging member 3 and by first and second walls 115a and 116a. Channel 114b is delimited by a portion of the base 113 of the interconnecting bridging member 7 and by first and second walls 115b and 116b. Each of walls 115a and 115b extend in an upward direction from the base 113 with each of the walls 116a and 116b being respectively connected to walls 115a and 115b and extending over at least a portion of the base 113. According to one implementation, walls 115a, 116a and walls 115b, 116b form L-shaped members as shown in the figures. It is important to note that the wall or walls that form the channels 114a and 114b may comprise other shapes and angular orientations.

According to one implementation the male portion 112 includes a central body 112a with first and second flange sections 118a and 118b extending from opposite sides of the central body. Each of the first and second flange sections 118a and 118b is provided with a surface 119a and 119b onto which is respectively supported elongate elastomeric members 120a and 120b that are at least in part elastically deformable. The elongate elastomeric members, like the other parts of the sternal closure assembly, are preferably made of a hypoallergenic material. According to some implementations the channels 114a, 114b and the elastomeric members 120a and 120b extend along at least a majority of the length of their respective interconnecting bridge members 3 and 7. The dimensional characteristics of the male portion 111 are such that the elongate members 120a and 120b must be at least partially compressed for the male portion 112 to be fitted into the female portion 111. As a result of being resilient, when the elastically deformable members 120a and 120b are in their compressed state they are internally urged to at least in part assume their original shape. This causes a forceful engagement between the female and male portions 111 and 112 which assist in holding the second sliding body 2 onto the first sliding body 1.

FIG. 4B shows the male portion 112 as it is being introduced into the female portion 111. In the implementation shown, the elongate elastically deformable member 120b includes a leading end 130 that has a height that is equal to or less than the height H1 of the channel 114b of the female portion 112. This facilitates an easy introduction of the deformable member 120b into the channel 114b. As shown in FIG. 4B, the height of the deformable member 120b may increase in a ramped fashion to a height H2 as measured from the base of the male portion 112. The sections of the deformable member 120b having a height greater than H1 are thereby compressed to assume the height H1 as it is introduced into the channel 114b. As explained above, because the elastically deformable members 120a and 120b are continuously being internally urged to assume, at least in part, their original shape, a forceful engagement between the female and male portions is achieved to assist in holding the second sliding body 2 onto the first sliding body 1.

As shown in FIGS. 4A and 4B, according to some implementations, an upper portion of the central body 12A of the male portion 112 resides within a central cavity 122 of the female portion 111 and has a height H3 greater than the height H1. According to some implementations the width of the upper portion of central body is slightly less than or equal to the width of the cavity 122 when the female portion 111 is not assembled with the male portion 112. This height and width of the central body can assist in maintaining a longitudinal alignment of the female and male portions 111 and 112 as the first and second sliding bodies 1 and 2 are telescopically mated.

According to some implementations the female portion 111 is constructed such that the channels 114a and 114b maintain their shape when the elongate members 120a and 120b of the male portion 112 are introduced into their respective channels. According to other implementations, as shown in FIG. 4A, the female portion 111 is constructed to also elastically deform with one or more of the walls that form the channels 114a, 114b bending outward in the direction C as the elongate elastomeric members 120a and 120b are introduced into the channels. For example, walls 116a and 116b may bend resiliently upward in the direction B and/or walls 115a and 115b may bend resiliently outward in the direction C. This bending of the walls can result in the formation of additional forces to assist in maintaining the first and second sliding bodies 1 and 2 in a fixed relationship with one another upon them being telescopically mated. For example, as shown in FIG. 4A, the bending of at least some of the walls 115a, 115b, 116a, 116b can cause the base 113 to flex in an upward direction D to cause the upper surface 140 of the base 113 to be forced against the bottom surface 141 of the male portion 112. This same phenomenon is applicable to the implementations of FIGS. 1-3 discussed above.

Figure 7:
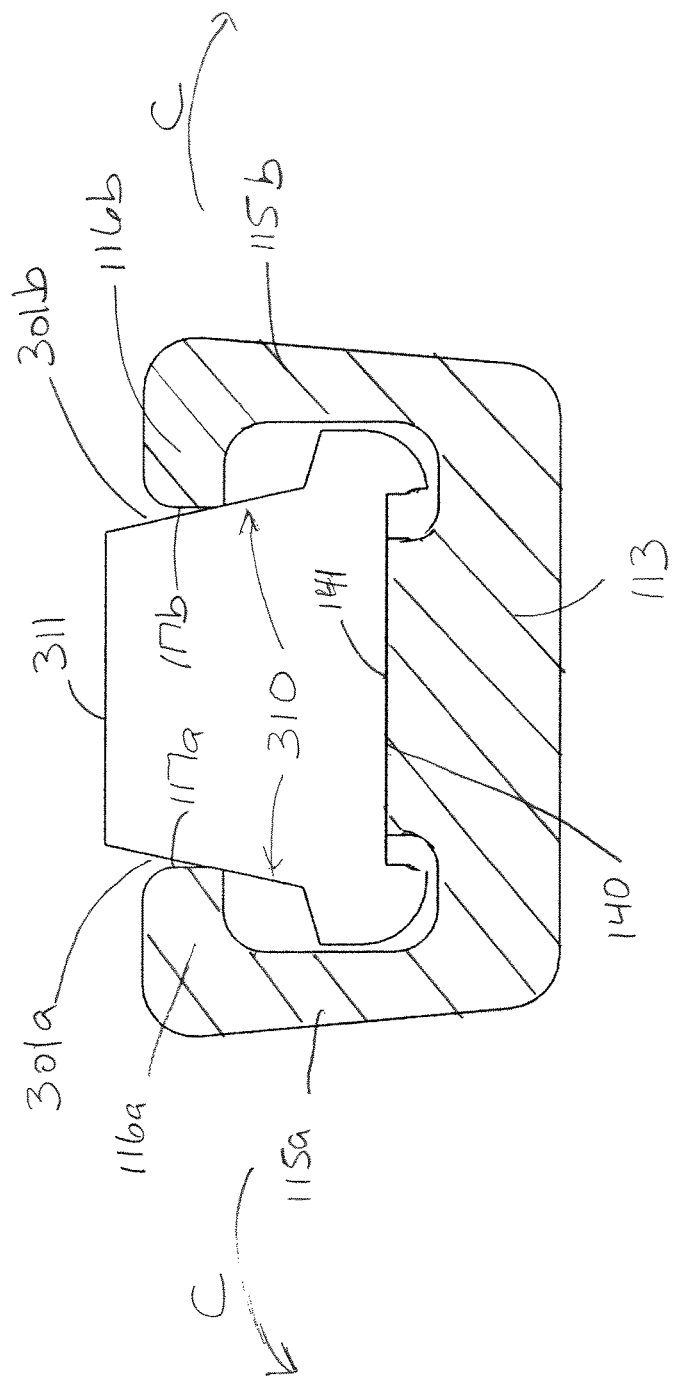
FIG. 7 shows a cross-section view of female and male portions according to another implementation.

As noted above, according to some implementations the upper portion of the central body 112A of the male portion 112 has a width slightly less than or equal to the width of the cavity 122 when the female portion 111 is not assembled with the male portion 112. However, according to other implementations the width of at least one section of the upper portion is greater than the width of the cavity 122 when the female portion 111 is in a rest state (i.e. when the female portion 111 is not assembled with the male portion 112). As shown in FIG. 7, this feature alone may be employed to cause an outward resilient bending of the arms 115a, 115b in the direction C, which may in turn result in a flexing of the base 113 in an upward direction D. As explained above, this flexing of the base 113 advantageously causes the upper surface 140 of the base 113 to be forced against the bottom surface 141 of the male portion 112. It is important to note that this feature may be employed alone, as in FIG. 7, or may be integrated with the other aspects of the sternal closure assemblies of FIGS. 1-5.

As shown in FIG. 7, according to some implementations the outer side walls 301a and 301b of the male portion 111 are inclined with the width dimension of a lower end portion 310 of the central body being greater than the width at the top end 311. Pursuant to such a construction, the contact surface between the side walls 301a and 301b and respective end walls 117a and 117b is minimized as a result of the different angular orientations of side walls 301 and end walls 117. This minimization of the contact surface between the male portion 112 and female portion 111 reduces frictional forces between the two as they are telescopically mated, thereby reducing the amount of force required to assemble the male portion 112 with the female portion 111.

Figure 8:
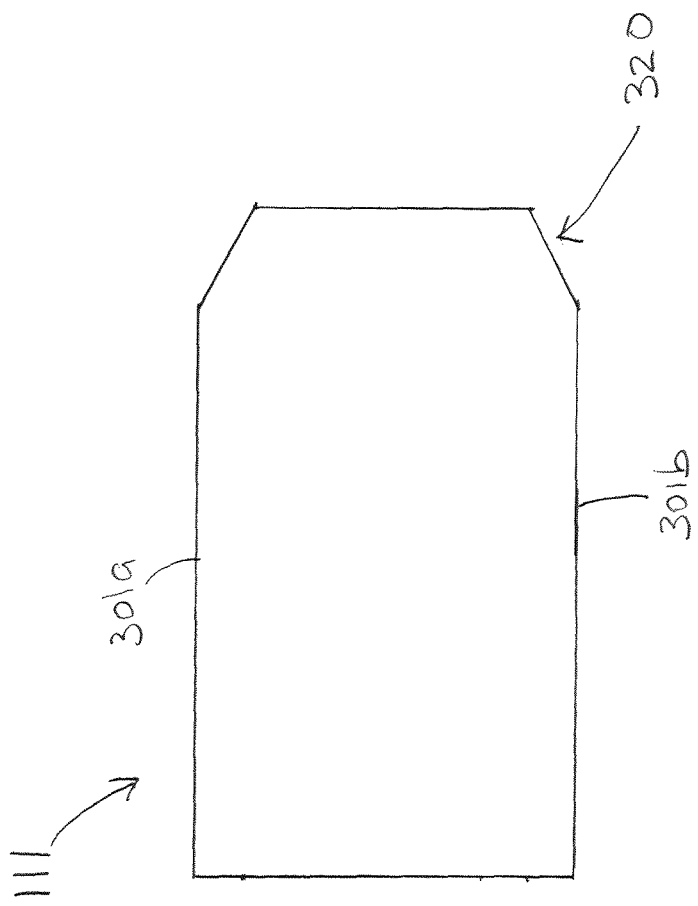
FIG. 8 illustrates a top view of a male portion according to some implementations.

According to some implementations the distance between the outer side walls 301a and 301b of the central body of the male portion 111 differ along its length as shown in FIG. 8. FIG. 8 shows a top view of the male portion 111 depicted in FIG. 7 according to one implementation. The leading end 320 of the male portion has a width that is less than the distance between the end walls 117a and 117b of the female portion 111 when the female portion is in a rest state (i.e. when the male portion 112 is not assembled in the female portion 111). This facilitates an easier initial introduction of the male portion 112 into the female portion 111. Distal to the leading end 320, the distance between the side walls 301a and 301b is greater than the distance between the end walls 117a and 117b of the female portion 111 when the female portion is in the rest state. According to some implementations the distance between the outer side walls 301a and 301b increases in a ramp-like fashion as depicted in FIG. 8.

FIGS. 5A and 5B illustrate another implementation wherein the elongate elastomeric members 120a and 120b are attached to the inner surface of channels 114a and 114b, respectively, of the female portion 111 rather than being attached to the male portion 112. The male portion 112 includes flange sections 170a and 170b extending from each side of the central body 112A that are configured to interact with respective elongate elastomeric members 120a and 120b in order to assist in holding the first and second sliding bodies 1 and 2 together during and after a telescopic coupling of the male portion 112 with the female portion 111. Like the implementations described above and below, the first and second sliding bodies 1 and 2 are assembled by sliding the male portion 112 lengthwise into the female portion 111. In the implementation depicted in FIGS. 5A and 5B at least a portion of the flange sections 170a and 170b has a height H1 that is greater than the height H2 of the channels 114a and 114b. Thus, as the flange sections 170a, 170b are introduced into channels 114a, 114b, the flange sections 170a, 170b retain their shape while the elongate elastomeric members 120a, 120b are compressed. This results in a forceful engagement between the female and male portions 111 and 112 that assists in holding the first and second sliding together both during and after the telescopic mating process.

FIG. 5B is a perspective view of one side of the sternal closure assembly at a point in time that the leading end 172 of the flange section 170b is being introduced into channel 114b. According to the implementation of FIG. 5B, to facilitate an easy introduction of the flange section into the channel 114b, the height of the leading end 172 is approximately the same or less than the height H2 of the channel 114b. Proceeding along the length of the flange section 170b in a direction toward the trailing end 9 of the second sliding member 2, the height of the flange section increases at least initially in a ramped fashion (via ramp 171) to the height H1.

Figure 6:
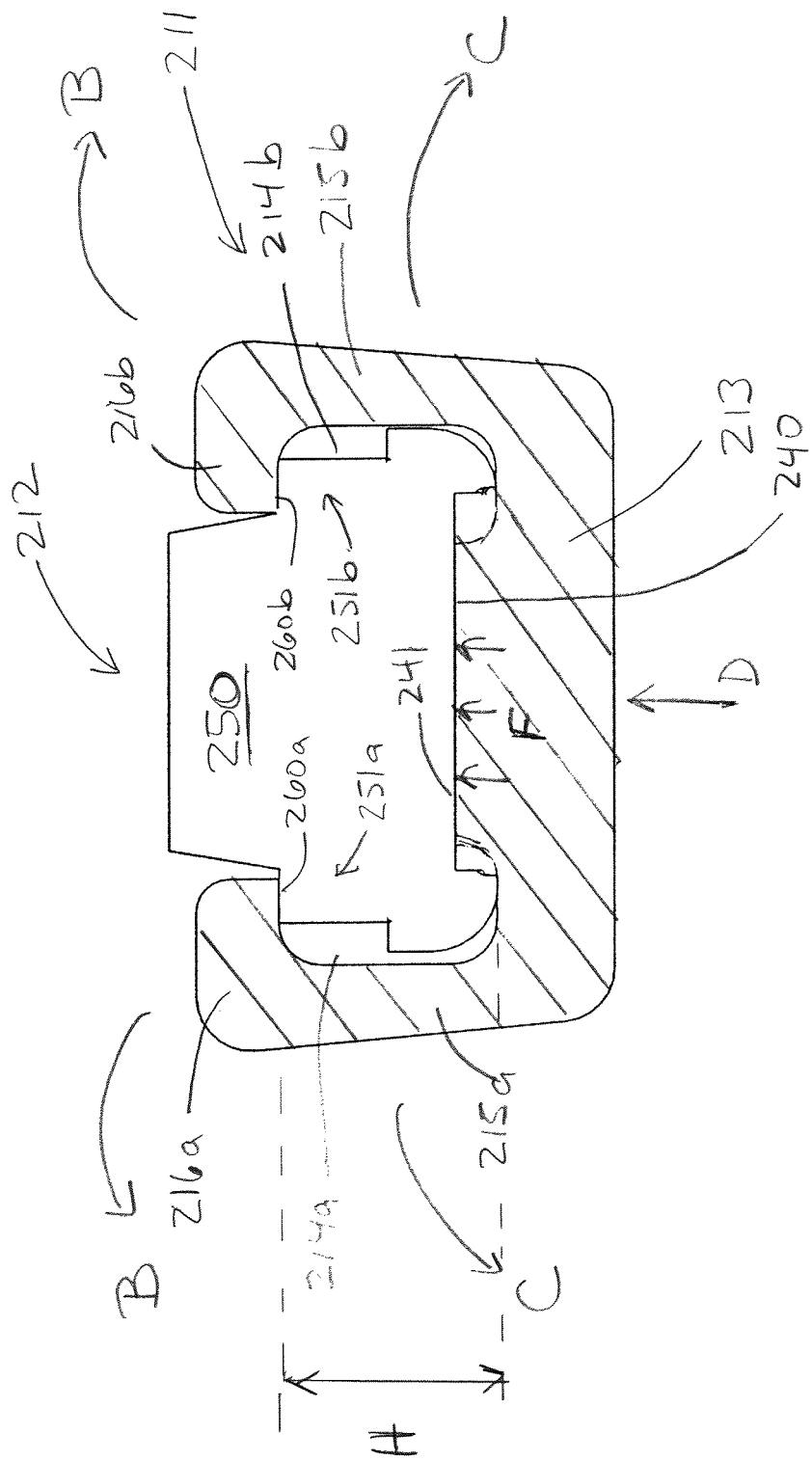
FIG. 6 shows a cross-section view of female and male portions according to another implementation.

FIG. 6 illustrates another implementation wherein the male portion 212 is made of a material that does not deform when introduced into the female portion 211. The female portion 211 includes two opposing facing channels 214a and 214b having one or more walls that are elastically deformable upon the male portion 212 being introduced into the female portion 211. Channel 214a is delimited by a portion of the base 213 of the longitudinal upper section and by first and second walls 215a and 216a. Channel 214b is delimited by a portion of the base 213 of the longitudinal upper section and by first and second walls 215b and 216b. Each of walls 215a and 215b extend in an upward direction from the base 213 with each of the walls 216a and 216b being respectively connected to walls 215a and 215b and extending over at least a portion of the base 213. As noted above, at least one of walls 215a and 216a and at least one of walls 215b and 216b is elastically deformable in order to enable the size of the channels 214a and 214b to be enlarged as the male portion 212 is introduced into the female portion 212. According to one implementation, walls 215a, 216a and walls 216b, 216b form L-shaped members as shown in FIG. 5. It is important to note that the wall or walls that form the channels 214a and 214b may comprise other shapes and angular orientations.

According to one implementation the male portion 212 includes a central body 250 having first and second flange sections 251a and 251b. Each of the first and second flange sections 251a and 251b is provided with a surface 260a and 260b onto which is respectively supported at least a portion of walls 216a and 216b when the first and second bodies 1 and 2 of the sternal closure assembly are telescopically mated. When the female portion is in a rest state, the height of the channels 214a and 214b is less than the height H of the respective flange sections 251a and 251b. When the first and second bodies 1 and 2 are assembled together one or more of the walls that delimit the channels 214a and 214b bend resiliently outward to permit the male portion 212 to be introduced into the female portion 111. This causes a contact force to exist between the flange surfaces 260a and 260b and the inner surface of the respective walls 216a and 216b that are supported thereon.

Like the implementation illustrated in FIG. 4B, the first and second flange sections 251a and 251b may have a profile similar to the elongate members 120a and 120b in that they may possess a leading end having a height that is equal to or less than the height of the respective channels 214a and 214b when the female portion 211 is in a rest state. This facilitates an easy introduction of the flange sections 251a and 251b into the respective channels 114a and 114b. Like in FIG. 4B, the height of the flange sections 251a and 251b may increase distally to the leading end in a ramped fashion.

According to some implementations the mechanical and dimensional characteristics of the female portion 211 and male portion 212 result in the walls 216a and 216b bending resiliently outward in the direction B and/or the walls 215a and 215b bending resiliently outward in the direction C. This can result in the formation of additional forces to assist in maintaining the first and second bodies 1 and 2 in a fixed relationship with one another upon them being telescopically mated. For example, as shown in FIG. 6, the outward bending of one or both of walls 215a and 215b can cause the base 213 to flex in an upward direction D to cause the upper surface 240 of the base 213 to be forced against the bottom surface 241 of the male portion 112.

Figure 9A:
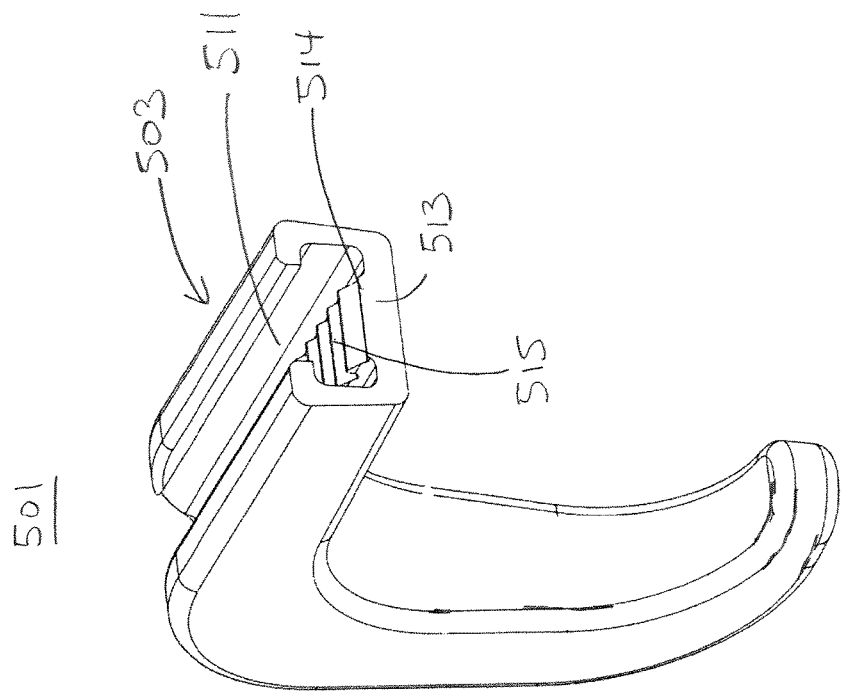
FIG. 9A shows a perspective view of a first sliding body of a sternal closure assembly according to one implementation, the first sliding body including an interconnecting bridge member with a plurality of upward projecting teeth arrange substantially transverse to the length of the interconnecting bridge member.
Figure 9B:
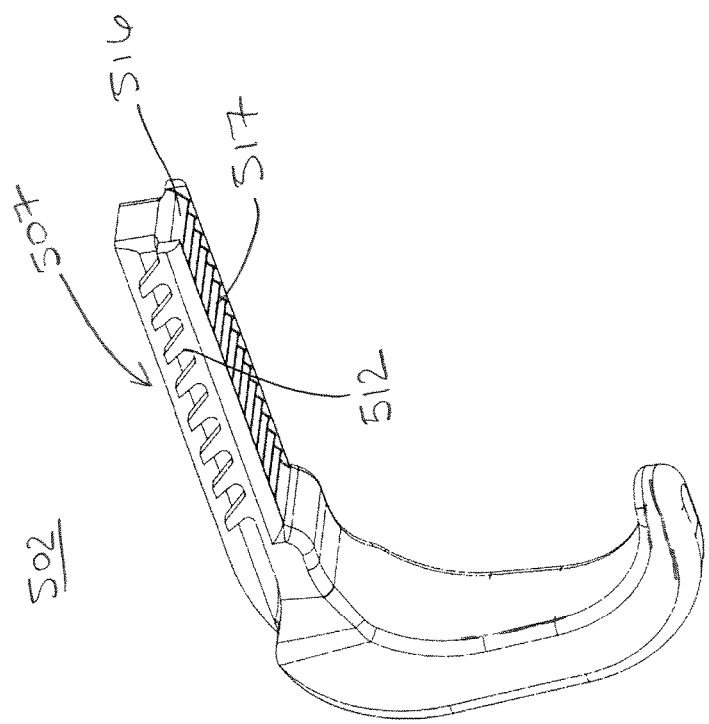
FIG. 9B shows a perspective view of a second sliding body of a sternal closure assembly according to one implementation, the second sliding body including an interconnecting bridge member with a plurality of downward projecting teeth arrange substantially transverse to the length of the interconnecting bridge member.
Figure 10:
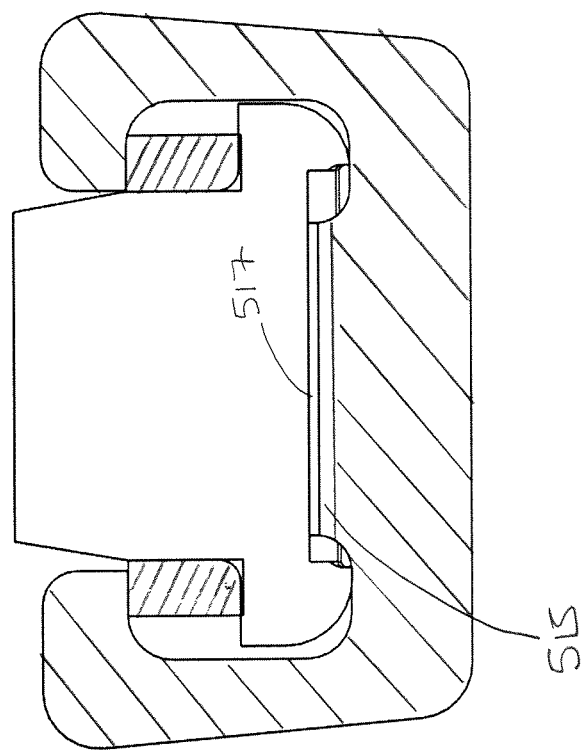
FIG. 10 shows a cross-section view of female and male portions useable to provide a forceful engagement between the plurality of downward and upward projecting teeth according to another implementation.
Figure 11:
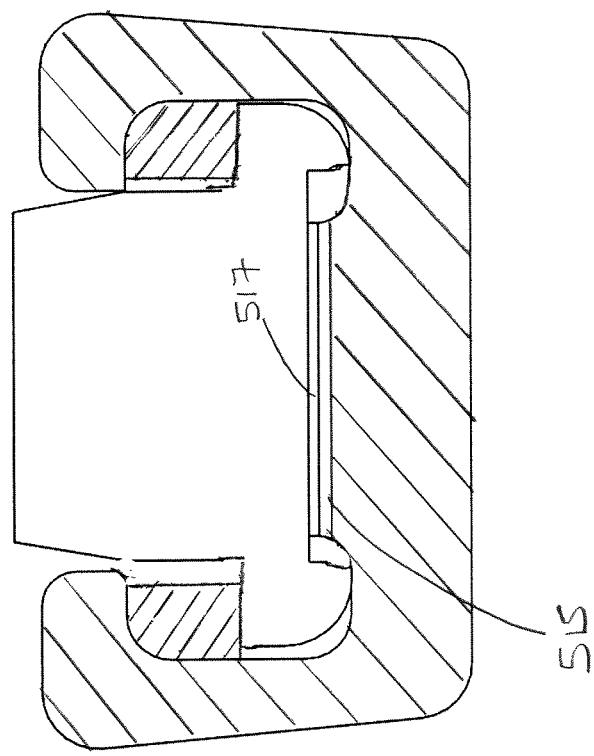
FIG. 11 shows a cross-section view of female and male portions useable to provide a forceful engagement between the plurality of downward and upward projecting teeth according to another implementation.
Figure 12:
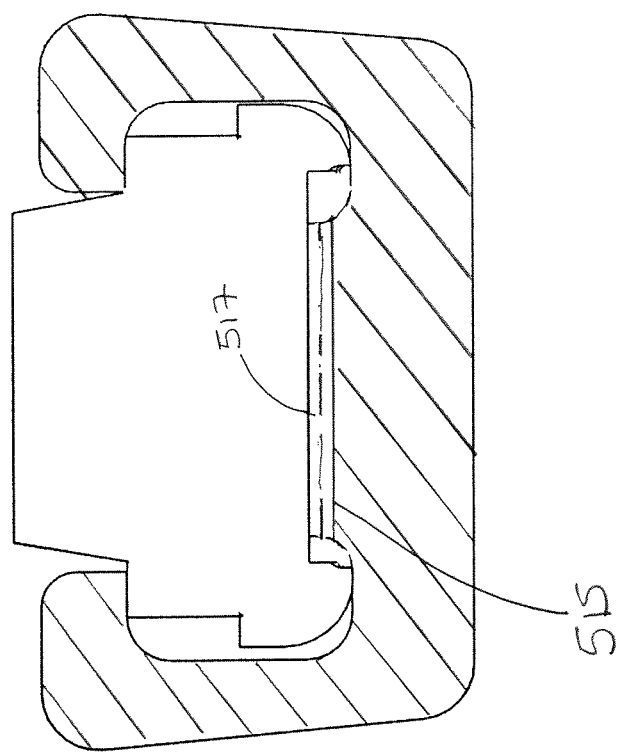
FIG. 12 shows a cross-section view of female and male portions useable to provide a forceful engagement between the plurality of downward and upward projecting teeth according to another implementation.
Figure 13:
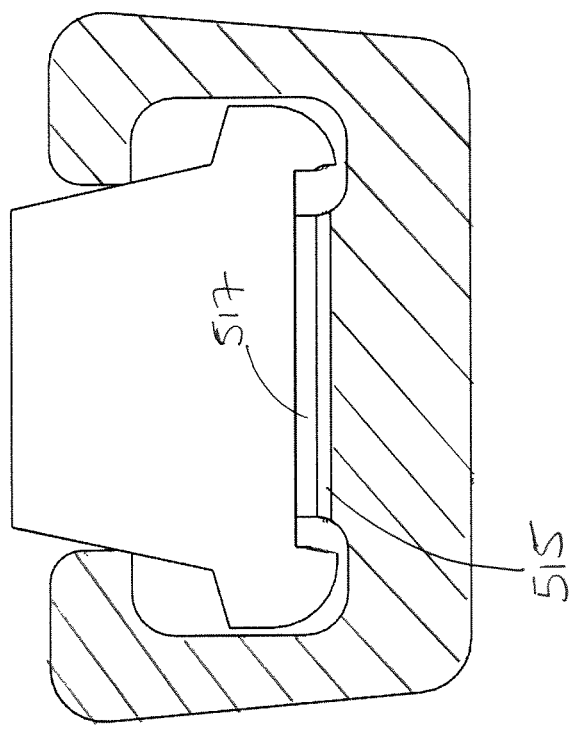
FIG. 13 shows a cross-section view of female and male portions useable to provide a forceful engagement between the plurality of downward and upward projecting teeth according to another implementation.

FIGS. 9A and 9B respectively illustrate first and second sliding bodies 501 and 502 of a sternal closure assembly according to another implementation. The first and second sliding bodies 501 and 501 are similar to the first and second sliding bodies 1 and 2 depicted in FIGS. 1A and 1B. The assembly differs in that the base 513 of the first interconnecting bridge member 503 has a top side 514 comprising a plurality of upward projecting teeth 515 arranged substantially transverse to the length of the first interconnecting bridge member. The assembly also differs in that the bottom side 516 of the second interconnecting bridge member 507 comprises a plurality of downward projecting teeth 517 arranged substantially transverse to the length of the second interconnecting bridge member and engageable with the plurality of upward projecting teeth 515. When the first and second sliding members are mated, or being telescopically mated, the plurality of upward projecting and downward projecting teeth 515 and 517 are configured to engage with one another in a manner that only permits a telescopic shortening of the sternal closure assembly when the first and second sliding members are mated, or being telescopically mated, the plurality of upward projecting and downward projecting teeth are configured to engage with one another in a manner that only permits a telescopic shortening of the sternal closure assembly without there being a change in the position of the plurality of upward projecting teeth 515 in relation to the base 513 of the first interconnecting bridge member 503 nor a change of position of the plurality of downward projecting teeth 517 in relation to the bottom side 516 of the second interconnecting bridge member 507. Like with the implementation of FIGS. 1-3, the male portion 512 is capable of being introduced into the female portion 511 only upon there being an elastic deformation of at least a part of at least one of the male and female portions. The male and female portions are configured such that when the second sliding body 502 is mated with the first sliding body 501 the elastic deformation results in a forceful engagement between the male and female portions and also in a forceful engagement between the pluralities of upward projecting teeth 115 and downward projecting teeth 117.

Each of the implementations of FIGS. 10-13 is respectively similar to each of the implementations of FIGS. 4-7 discussed above. The implementations of FIGS. 10-13 differ in the first interconnecting bridge member comprises a plurality of upward projecting teeth 515 and the second interconnecting bridge member 507 comprises a plurality of downward projecting teeth 517 engageable with the plurality of upward projecting teeth 515 as described in the preceding paragraph. Hence the male and female portions of the respective implementations of FIGS. 10-13 are configured such that when the second sliding body 502 is mated with the first sliding body 501 the elastic deformation results in a forceful engagement between the male and female portions and also in a forceful engagement between the plurality of upward projecting teeth 115 and downward projecting teeth 117.

Numerous exemplary implementations have been disclosed and described herein. It is to be appreciated however, that the present invention is in no way to be construed as to being limited to these examples.

What is claimed is:

1. A sternal closure assembly for securing first and second lateral halves of a sternum that has been longitudinally severed, the sternal closure assembly comprising:
   a first sliding body member including a first interconnecting bridge member and at least one leg extending downwardly from the first interconnecting bridge member, the at least one leg configured to abut an exterior edge of the first lateral halve of the sternum, the first interconnecting bridge member having a length and comprising a female portion, the female portion delimited in part by a base of the first interconnecting bridge member, the base including a top side comprising a plurality of upward projecting teeth arranged substantially transverse to the length of the first interconnecting bridge member; and
   a second sliding body telescopically mateable with the first sliding body, the second sliding body including a second interconnecting bridge member and at least one leg extending downwardly from the second interconnecting bridge member, the at least one leg configured to abut an exterior edge of the second lateral halve of the sternum, the second interconnecting bridge member having a length and comprising a male portion, the second interconnecting bridge member having a bottom side comprising a plurality of downward projecting teeth engageable with the plurality of upward projecting teeth, the plurality of downward projecting teeth arranged substantially transverse to the length of the second interconnecting bridge member,
   when the first and second sliding bodies are mated, or being telescopically mated, the plurality of upward projecting and downward projecting teeth are configured to engage with one another in a manner that only permits a telescopic shortening of the sternal closure assembly without there being a change in the position of the plurality of upward projecting teeth in relation to the first interconnecting bridge member nor a change of position of the plurality of downward projecting teeth in relation to the second interconnecting bridge member, the male portion capable of being introduced into the female portion only upon there being an elastic deformation of at least a part of at least one of the male and female portions, the male and female portions configured such that when the second sliding body is mated with the first sliding body the elastic deformation results in a forced engagement between the male and female portions and also in a forced engagement between the plurality of upward projecting teeth and downward projecting teeth.

2. The sternal closure assembly according to claim 1, wherein the female portion comprises a channel delimited by at least one wall, the at least one wall configured to elastically deform by bending outward when the male portion is introduced into the female portion.

3. The sternal closure assembly according to claim 1, wherein the female portion comprises a channel delimited by at least a first wall and a second wall, the first wall extending from the base of the first interconnecting bridge member, the second wall connected to the first wall and extending over at least a portion of the base, the first wall configured to elastically deform by bending outward when the male portion is introduced into the female portion.

4. The sternal closure assembly according to claim 1, wherein the female portion comprises a channel delimited by at least a first wall and a second wall, the first wall extending from a base of the first interconnecting bridge member, the second wall connected to the first wall and extending over at least a portion of the base, the second wall configured to elastically deform by bending outward when the male portion is introduced into the female portion.

5. The sternal closure assembly according to claim 1, wherein the female portion comprises a channel delimited by at least a first wall and a second wall, the first wall extending from a base of the first interconnecting bridge member, the second wall connected to the first wall and extending over at least a portion of the base, each of the first and second walls being configured to elastically deform by bending outward when the male portion is introduced into the female portion.

6. The sternal closure assembly according to claim 1, wherein the female portion comprises a channel delimited by at least an L-shaped wall, the L-shaped wall including a first segment that extends substantially orthogonally from a base of the first interconnecting bridge member and a second segment connected to the first segment that extends over at least a portion of the base, the L-shaped wall configured to elastically deform such that at least one of the first and second segments bends outward when the male portion is introduced into the female portion.

7. The sternal closure assembly according to claim 1, wherein the male portion is configured to elastically deform and the female portion is configured not to deform when the male portion is introduced into the female portion.

8. The sternal closure assembly according to claim 1, wherein the female portion is configured to elastically deform and the male portion is configured not to deform when the male portion is introduced into the female portion.

9. The sternal closure assembly according to claim 1, wherein both the male portion and the female portion are configured to elastically deform when the male portion is introduced into the female portion.

10. The sternal closure assembly according to claim 1, wherein the male portion comprises an elastomeric member, the male portion having dimensional characteristics that require the elastomeric member to be at least partially compressed to fit within the female portion.

11. The sternal closure assembly according to claim 10, wherein the male portion includes a first part that is configured not to deform when the male portion is introduced into the female portion, the elastomeric member formed separately from the first part and being attached to the first part.

12. The sternal closure assembly according to claim 1, wherein the female portion comprises an elastomeric member, the male portion having dimensional characteristics that require the elastomeric member to be at least partially compressed for the male portion to fit within the female portion.

13. The sternal closure assembly according to claim 12, wherein the female portion includes a first part that is configured not to deform when the male portion is introduced into the female portion, the elastomeric member formed separately from the first part and being attached to the first part.

14. The sternal closure assembly according to claim 1, wherein the female portion comprises a channel configured to receive a part of the male portion, the channel being delimited by at least an upper wall and a lower wall and having a first height dimension, the male portion including a plurality of elastically deformable, spaced-apart tabs that extend substantially orthogonally from a base of the second interconnecting bridge member, the male portion having a second height dimension greater than the first height dimension prior to the male portion being introduced into the channel, the plurality of tabs configured to bend in a direction toward the base when the part is introduced into channel.

15. The sternal closure assembly according to claim 14, wherein at least some of the plurality of tabs include a leading edge in the form of a ramp having a forward end and a trailing end, the forward end having a height less than the height of the trailing end.

16. The sternal closure assembly according to claim 1, wherein
the female portion comprises:
first and second wall segments extending respectively from first and second sides of a base of the first interconnecting bridge member,
a third wall segment connected to the first wall segment and forming with the base and first wall segment a first elongate channel, the third wall segment extending at least partially over the base,
a fourth wall segment connected to the second wall segment and forming with the base and second wall segment a second elongate channel, the fourth wall segment extending at least partially over the base,
a gap existing between the third and fourth wall segments, the gap having a width,
the male portion comprises:
a first part configured to reside within the first channel when the second sliding body is telescopically mated with the first sliding body,
a second part configured to reside within the second channel when the second sliding body is telescopically mated with the first sliding body,
a third part coextensive with and located between the first and second parts, the third part having first and second opposing side walls that are separated by a distance, the distance being greater than the width of the gap.

17. The sternal closure assembly according to claim 16, wherein one or both of the first and second wall segments of the female portion are configured to elastically deform by bending outward when the male portion is introduced into the female portion.

18. The sternal closure assembly according to claim 1, wherein the first interconnecting bridge member comprises a base having a first side and a second side, the female portion having first and second substantially L-shaped members extending from the respective first and second sides, the first and second substantially L-shaped members forming with the base first and second elongate channels, each of the first and second substantially L-shaped members having a first wall segment extending from the base and a second wall segment connected to the first wall segment, each of the second wall segments extending at least partially over the base with there being a gap existing between the second wall segments, the base and each of the second wall segments separated by a first height dimension, the male portion comprising first and second elongate members configured to respectively reside inside the first and second elongate channels of the female portion when the first and second sliding bodies are telescopically mated, each of the first and second elongate members including a leading section in the form of a ramp having a first end and a second end, the first end having a height dimension less than the first height dimension, the second end having a height dimension greater than the first height dimension.

19. The sternal closure assembly according to claim 18, wherein each of the first and second elongate members comprise an elastomeric material and have dimensional characteristics that require a compression of the elastomeric material for the first and second elongate members to be fitted into the respective first and second channels.

20. The sternal closure device according to claim 18, wherein at least a part of the female portion is configured to elastically deform and the male portion is configured not to deform when the male portion is introduced into the female portion.

21. The sternal closure device according to claim 18, wherein each of the first and second elongate members of the male portion are configured to elastically deform when the male portion is introduced into the female portion.

22. The sternal closure device according to claim 21, wherein at least a part of the female portion is configured to elastically deform and each of the first and second elongate members of the male portion are configured to elastically deform when the male portion is introduced into the female portion.

* * * * *